(12) United States Patent
Frank et al.

(10) Patent No.: US 7,530,255 B2
(45) Date of Patent: May 12, 2009

(54) DEVICES, SYSTEMS AND METHODS FOR TESTING OF GAS DETECTORS

(75) Inventors: William R. Frank, Pittsburgh, PA (US); Daniel E. Bruce, Murrysville, PA (US); Jon K. Haverstick, Butler, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 411 days.

(21) Appl. No.: 11/171,861

(22) Filed: Jun. 30, 2005

(65) Prior Publication Data

US 2006/0156789 A1 Jul. 20, 2006

(51) Int. Cl.
*G01N 37/00* (2006.01)
(52) U.S. Cl. ......................... 73/1.03; 73/1.06
(58) Field of Classification Search ......... 345/421–422, 345/426, 428, 581, 589, 639, 611–614; 382/254, 382/300, 266–269, 274–276; 73/1.03, 1.06, 73/1.07
See application file for complete search history.

(56) References Cited

U.S. PATENT DOCUMENTS 3,445,669 A * 5/1969 Erickson et al. ............. 250/577

(Continued)

FOREIGN PATENT DOCUMENTS

GB 1 389 453 4/1975

(Continued)

OTHER PUBLICATIONS

Daniel Wojtowicz: "Microdock II User Manual" [online]; Jan. 13, 2005; BW Technologies Ltd, Canada' XP002375024 Retrieved from Internet: URL:http://www.gasmonitors.com/main.cfm?sub3=216 &page=pdf&doc=2&pid=34 [retrieved on Mar. 30, 2006].

(Continued)

*Primary Examiner*—Hezron Williams
*Assistant Examiner*—Nashmiya S. Fayyaz
(74) *Attorney, Agent, or Firm*—James G. Uber; Henry E. Bartony, Jr.

(57) ABSTRACT

A testing module for use with a gas detector, includes a plurality of gas inlets and outlets, each outlet being in fluid connection with one of the inlets. Each of the outlets is adapted to mate with and form a fluid connection with one of the inlets of a second like testing module. Gases can then flow from the outlets of the testing module into the inlets of the second like testing module. A gas container module for use with a gas container, includes a plurality of gas inlets and outlets, each inlet being in fluid connection with one of the outlets. Each of the inlets is adapted to mate with and form a fluid connection with one of a the outlets on a second like gas container module. Gases can then flow from the outlets of the second like gas container module into the inlets of the gas container module.

23 Claims, 12 Drawing Sheets

U.S. PATENT DOCUMENTS

| | | | | |
|---|---|---|---|---|
| 4,142,860 A | * | 3/1979 | Mayeaux | 73/1.03 |
| 4,390,869 A | * | 6/1983 | Christen et al. | 340/632 |
| 5,818,456 A | * | 10/1998 | Cosman et al. | 345/614 |
| 6,237,392 B1 | * | 5/2001 | Yu et al. | 73/1.06 |
| 6,452,595 B1 | | 9/2002 | Montrym | |
| 6,469,707 B1 | | 10/2002 | Voorhies | |
| 6,720,975 B1 | | 4/2004 | Dietrich | |
| 6,999,100 B1 | * | 2/2006 | Leather et al. | 345/611 |
| 2003/0000281 A1 | | 1/2003 | Ketler et al. | |
| 2005/0000981 A1 | | 1/2005 | Peng et al. | |
| 2005/0189239 A1 | * | 9/2005 | Ellis et al. | 205/780.5 |
| 2006/0042353 A1 | * | 3/2006 | Marquis et al. | 73/23.2 |
| 2006/0103663 A1 | * | 5/2006 | Collodi | 345/611 |
| 2007/0097145 A1 | * | 5/2007 | Akenine-Moller | 345/611 |

FOREIGN PATENT DOCUMENTS

JP        2006003115 A   *   1/2006

OTHER PUBLICATIONS

MSA Instrument Division: "Galaxy Automated Test System User Manual" [online]; 2003, MSA Instrument Division, USA, XP002375025 Retrieved from the Internet: USL:http//media.msanet.com/NA/USA/PortableInstruments/CalibrationEquipment/GalaxyAutomatedTestSystem/10061049.pdf> [retrieved on Mar. 30, 2006].

* cited by examiner

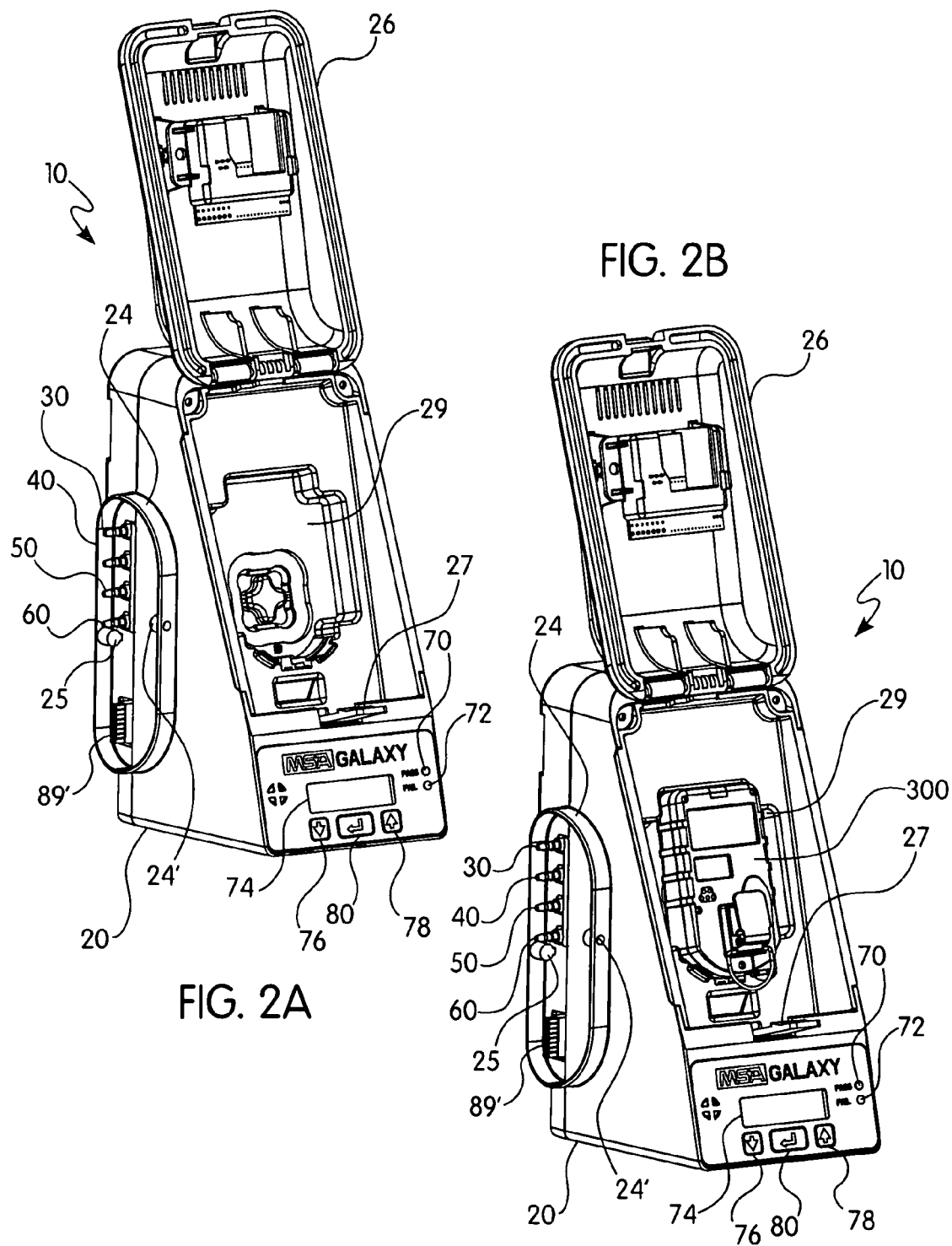

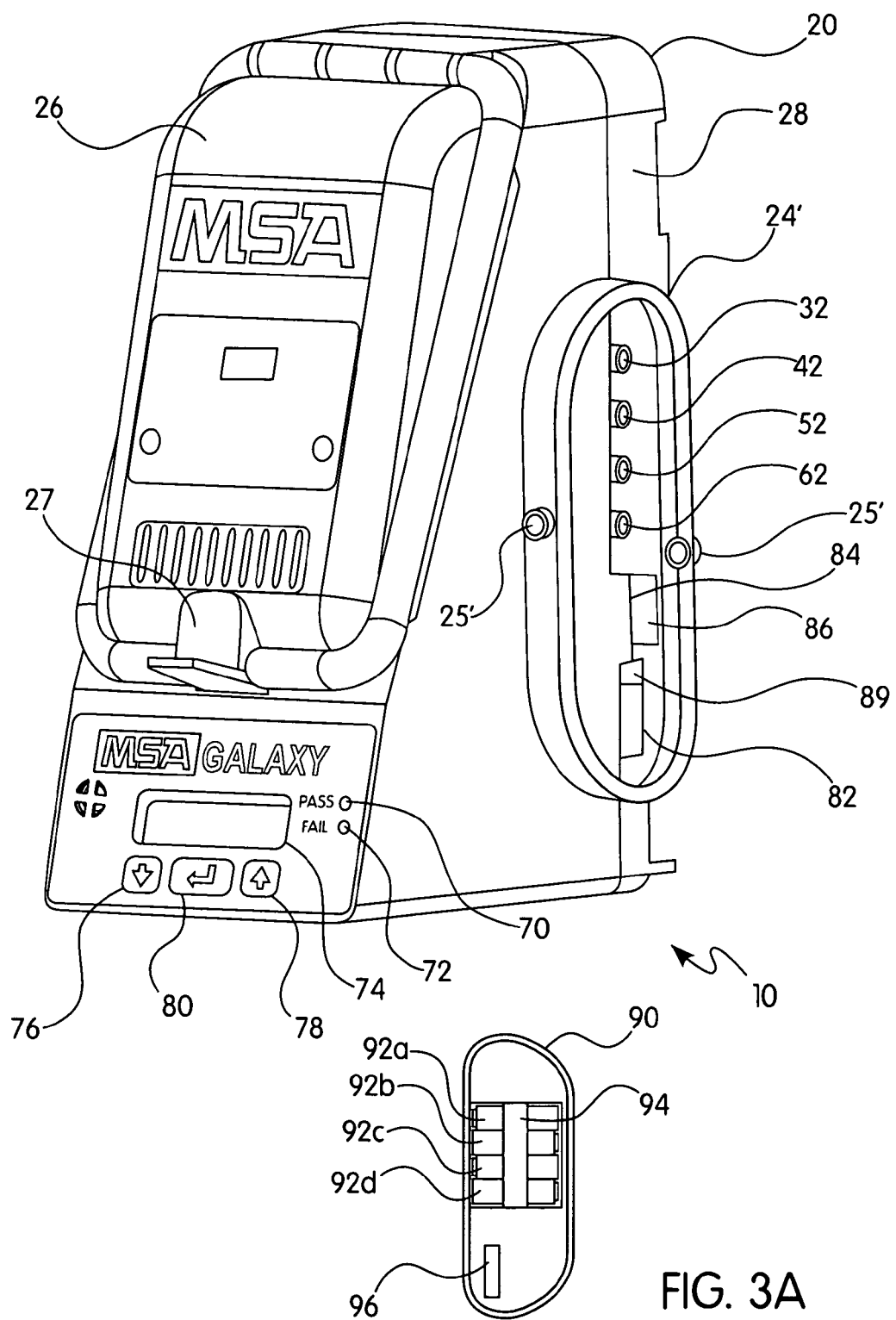

DEVICES, SYSTEMS AND METHODS FOR TESTING OF GAS DETECTORS

BACKGROUND OF THE INVENTION

The present invention relates generally to devices, systems and methods for the testing of gas detectors, and especially, to devices, systems and methods for calibrating or testing a response of one or more gas sensors of one or more gas detectors to one or more analyte test gases.

Gas detectors including one or more gas sensors (for example, electrochemical gas sensors, combustible gas sensors, etc.) are well known for monitoring for potentially hazardous gases in various environments. Generally, gas from the environment to be monitored comes into contact with the sensors(s) within the detector by diffusion or by forced flow. Electronics within the detector convert the output signal from the sensor(s) into one or more signals representative of a gas concentration. The sensor output per unit amount of gas can vary with time and hence periodic calibration is required to ensure that the detector reading is accurate.

Currently, sensors of gas detectors are calibrated by passing a calibration gas having known, fixed compositions of one or more analyte gases from a compressed gas cylinder into the detector, thereby displacing ambient air within the detector and exposing the sensor(s) to the calibration gas. The calibration gas is allowed to flow until the sensor output reaches a steady state. Since the calibration gas has a known composition, the output signal from each sensor of the gas detector can be adjusted to provide an accurate measure of analyte gas concentration. Excess calibration gas flows out of the detector. In the interval between full calibrations, an intermediate test (sometimes referred to as a bump test) can be performed to ensure that a sensor or instrument is responding to a specific analyte test gas. As used herein, the term "testing" refers generally to all types of analysis of the operation of a gas detector and includes, for example, full calibration and bump testing.

Safe commercial practice dictates that sensors within a gas detector be tested, including calibrated, at a minimum according to the manufacturer's recommendations. Various calibration/testing systems and methods have been developed to facilitate gas detector testing. Gas detector calibration/testing systems are disclosed, for example, in U.S. Pat. Nos. 5,239,492, 4,854,153 and 5,655,894. European patent No. EP 1 342 082 discloses a calibration system for use with a portable gas detector.

Moreover, several calibration/testing systems are commercially available in the United States. For example, the MICRODOCK™ automatic test and calibration station available from BW Technologies of Canada provides a calibration and bump testing station for the GasAlertMicro™ multi-gas detector. One inlet is provided for ambient air, and another inlet is provided for connection to a single pressurized gas cylinder. As described in the MicroDock Automating Test and Calibration Station User Manual (2103) available from BW Technologies, multiple gas detector docking modules can be connected to the system. However, test gas can flow to only one connected docking module at a time and thus only one gas detector can be calibrated at any one time. Also, the TIM® Total Instrument Manager calibration/testing system is available from Mine Safety Appliances Company of Pittsburgh, Pa., which provides, among other functions, full calibration and bump testing for several Mine Safety Appliances Company gas detectors, including multi-gas instruments and single gas monitors.

Although strides have been made in facilitating testing of gas detectors, a number of problems still persist. Among other problems, currently available calibration systems can require time consuming changes in connections of gas cylinders and gas detectors as well as changes in test conditions to test a single or multiple gas detectors with one or more test gases.

It thus remains desirable to develop improved (for example, more automated) devices, systems and methods for testing of gas detectors.

SUMMARY OF THE INVENTION

In one aspect, the present invention provides a testing module for use with a gas detector, including: a housing; a seating connected to the housing and adapted to operably connect the gas detector to the testing module; a plurality of gas inlets connected to the housing, each gas inlet adapted to pass a gas therethrough; and a plurality of gas outlets connected to the housing, each gas outlet being in fluid connection with one of the gas inlets. The plurality of gas outlets are configured on the housing in generally the same configuration as the plurality of inlets are configured on the housing. Further, each of the plurality of outlets is adapted to mate with and form a fluid connection with one of a plurality of inlets of a second like testing module. Once such fluid connections are made, gases can flow from the outlets of the testing module into the inlets of the second like testing module.

The testing module can further include a communication system to receive information and/or to transmit information. The communication system can be provided to transmit and receive communications between the testing module and the second like testing module when connected. The testing module can also include a data input system and a data output system. The testing module can further include a flow control system adapted to provide flow from at least one of the plurality of inlets to the gas detector.

In one embodiment, the plurality of inlets are configured in a generally linear configuration. Each of the plurality of inlets can, for example, include a barbed connector.

In another aspect, the present invention provides a gas container module for use with a gas container, including: a housing; a seating connected to the housing and adapted to receive the gas container; a plurality of gas inlets connected to the housing, each inlet adapted to pass a gas therethrough; and a plurality of gas outlets connected to the housing. Each inlet is in fluid connection with one of the outlets. The plurality of inlets are configured on the housing in generally the same configuration as the plurality of outlets are configured on the housing. Each of the plurality of inlets is adapted to mate with and form a fluid connection with one of a plurality of outlets on a housing of a second like gas container module. Once such fluid connections are made, gases can flow from the outlets of the second like gas container module into the inlets of the gas container module.

The gas container module can further include a gas container conduit in fluid connection with one of the outlets at a first end thereof. The gas container conduit is adapted to form a connection with the gas container at a second end thereof. The gas container module can also include a demand regulator in fluid connection with the second end of the gas container conduit.

In one embodiment there are at least X inlets $I_1$ through $I_x$ and at least X+1 outlets $O_1$ through $O_{x+1}$. The first end of the container conduit is in fluid connection with outlet $O_1$, and each inlet $I_i$ is in fluid connection with outlet $O_{i+1}$. In one embodiment, there are at least two inlets $I_1$ and $I_2$ and at three outlets $O_1$ through $O_3$, wherein the first end of the gas container conduit is in fluid connection with outlet $O_1$, inlet $I_1$ is in fluid connection with $O_2$ and inlet $I_2$ is in fluid connection with outlet $O_3$. In one embodiment, the outlet $O_1$ is adapted to mate with and form a fluid connection with inlet $I_1'$ of the second like gas container module and outlet $O_2$ is adapted to mate with and form a fluid connection with inlet $I_2'$ of the second like gas container module. The gas container module of can further include a connector to mate with and form a connection with outlet $O_3$. The gas container module can also include an air inlet connected to the housing and being in fluid connection with an air outlet connected to the housing The air inlet is adapted to mate and form a fluid connection with an air inlet of the second like gas container module.

The gas container module can further include a communication system. In one embodiment, the gas container includes a sensor in communicative connection with the communication system. The sensor is adapted to read data from the gas container.

In one embodiment, the plurality of inlets are arranged in a series on a first section of the housing of the gas container module and the plurality of outlets are arranged in a series in a second section of the housing of the gas container module. The gas container module can also include a container conduit in fluid connection with one of the outlets at a first end. The container conduit is adapted to form a connection with the gas container at a second end thereof. Each of the plurality of inlets is in fluid connection with one of the plurality of outlets such that when a plurality of like gas container modules are connected in a series, a gas exiting each outlet is determined by a position in the series of gas container modules of the one of the gas container modules seating a corresponding gas container.

In still a further aspect, the present invention provides a gas detector testing system, including at least one testing module for use with a gas detector as described above and at least one gas container module for use with a gas container as described above. In one embodiment, the testing module includes: a testing module housing; a seating connected to the testing module housing and adapted to operably connect the gas detector to the testing module; a plurality of inlets connected to the testing module housing, each inlet adapted to pass a gas therethrough; and a plurality of outlets connected to the testing module housing, each outlet being in fluid connection with one of the gas inlets. As described above, the plurality of outlets are configured on the testing module housing in generally the same configuration as the plurality of inlets are configured on the testing module housing. Each of the plurality of outlets is adapted to mate with and form a fluid connection with one of a plurality of inlets of a second like testing module. Once such fluid connections are made, gases can flow from the outlets of the testing module into the inlets of the second like testing module.

In this embodiment, the gas container module, includes: a gas container module housing; a seating connected to the gas container module housing and adapted to receive the gas container; a plurality of gas inlets connected to the gas container module housing, each gas inlet adapted to pass a gas therethrough; and a plurality of gas outlets connected to the gas container module housing, each gas inlet being in fluid connection with one of the gas outlets. The plurality of gas inlets are configured on the gas container housing in generally the same configuration as the plurality of gas outlets are configured on the gas container housing. Each of the plurality of gas inlets is adapted to mate with and form a fluid connection with one of a plurality of gas outlets on a gas container housing of a second like gas container module. Once such fluid connections are made, gases can flow from the gas outlets of the second like gas container module into the gas inlets of the gas container module.

The plurality of inlets of the testing module are also configured on the testing module housing in generally the same configuration as the plurality of gas outlets are configured on the gas container module housing. Further, each of the plurality of inlets of the testing module are adapted to mate with and form a fluid connection with one of the gas outlets of the gas container module. Once such fluid connections are made, gases can flow from the gas outlets of the gas container module into the inlets of the testing module.

BRIEF DESCRIPTION OF THE DRAWINGS

Other aspects of the invention and their advantages will be discerned from the following detailed description when read in connection with the accompanying drawings, in which:

FIG. 2A illustrates a perspective view of the testing module of FIG. 1 with the access door thereof in an open state.

FIG. 2B illustrates a perspective view of the testing module of FIG. 1 with the access door thereof in an open state with a gas detector placed in operative connection therewith.

FIG. 3A illustrates a side perspective view of the testing module of FIG. 1 from the opposite side of FIG. 1 and a side view of the battery pack of FIG. 1.

DETAILED DESCRIPTION OF THE INVENTION

In general, the devices, systems and methods of the present invention are discussed using representative embodiments in which three test gases and air are transported through the system of the present invention for the testing of gas detectors. One skilled in the art appreciates that the devices, systems and methods of the present invention are readily expanded to use more than three test gases and air. Likewise, the devices, systems and methods of the present invention are discussed using representative embodiments of systems in which a single gas container module as described herein is connected to a single testing module as described herein, or in which two or three gas container modules (connected in series) are connected to one testing module or to two testing modules (connected in series). One skilled in the art appreciates that the devices, systems and methods of the present invention are readily expanded to connect more than three gas container modules of the present invention and more than two testing modules of the present invention.

Figure 1:
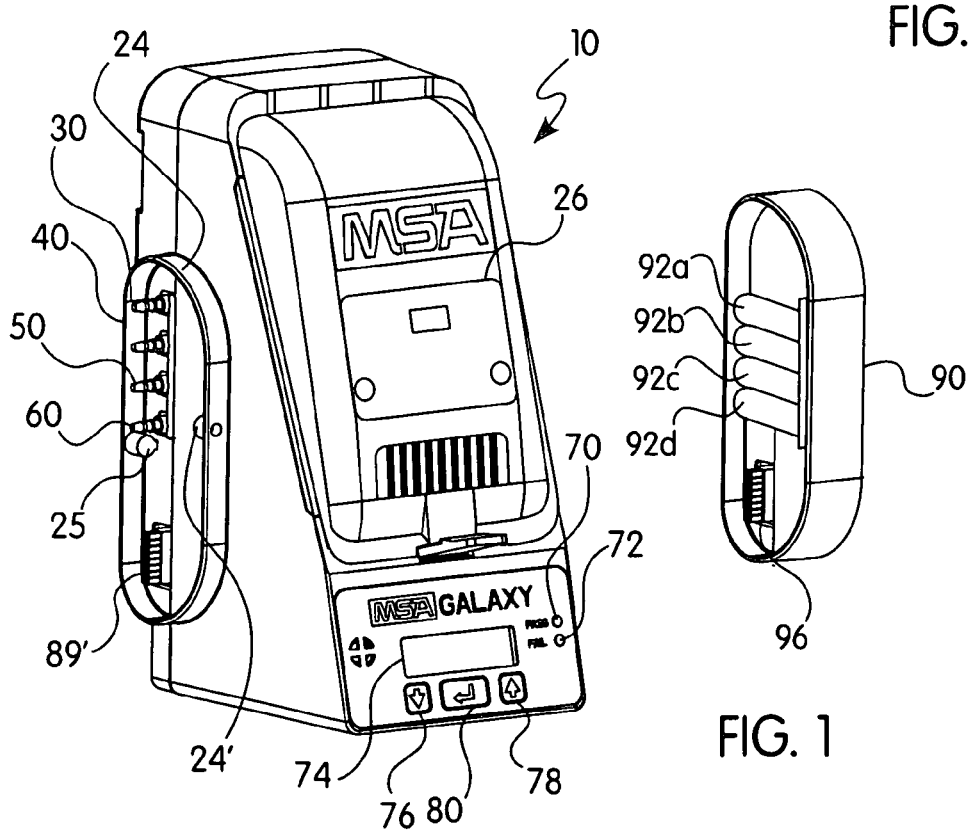
FIG. 1 illustrates a side perspective view of an embodiment of a testing module of the present invention with an embodiment of a battery pack in alignment for connection therewith.

FIG. 1 illustrates an embodiment of a gas detector testing module 10 of the present invention. Test stand or testing module 10 includes a plurality of inlets on a first side 22 of a housing 20 thereof. In the embodiment of FIG. 1, testing module 10 includes four inlets 30, 40, 50 and 60 arranged generally along a line at predetermined, unique positions (unique vertical positions in the orientation of FIG. 1) on housing 20. One skilled in the art will appreciate that virtually any number of inlets in a variety of configurations can be provided in the present invention. In the embodiment of FIG. 1, inlets 30, 40, 50 and 60 can, for example, comprise ⅛ inch barbed connectors as known in the gas connection arts. Inlets 30, 40, 50 and 60 are surrounded by a connecting and protecting flange 24, the operation of which is discussed below.

Testing module 10 further includes data input and output systems. For example, a pass indicator 70 and a fail indicator 72 (for example, LED indicators) are provided to indicate to an operator if a gas detector in operative connection with testing module 10 has passed or failed a particular test. Likewise, a display 74 is provided to display information to an operator. In the embodiment of FIG. 1, a menu of commands is provided on display 74 through which an operator can scroll and choose a command or commands using down, up and enter controls 76, 78 and 80, respectively. Housing 10 further includes a hinged access door 26 through which a gas detector 300 can be placed in a seating 29 of testing module 10 for operative connection with testing module 10 (see, for example, FIGS. 2A and 2B). Housing 20 can further include a latch system 27 as known in the art to maintain access door 26 in a closed state.

Figure 3B:
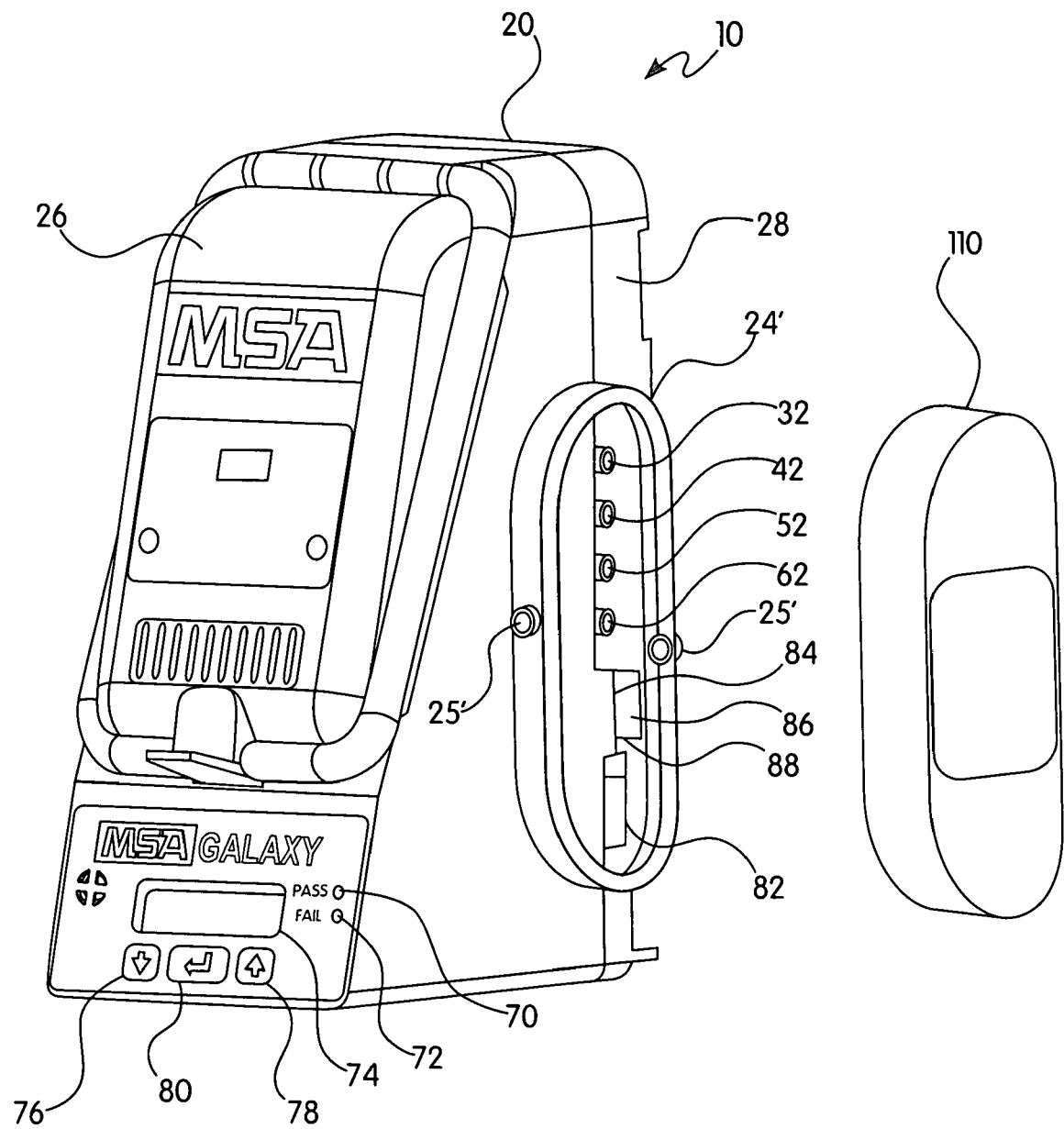
FIG. 3B illustrates a side perspective view of the testing module of FIG. 1 from the opposite side of FIG. 1 with an embodiment of an end cap in alignment for attachment thereto.
Figure 5A:
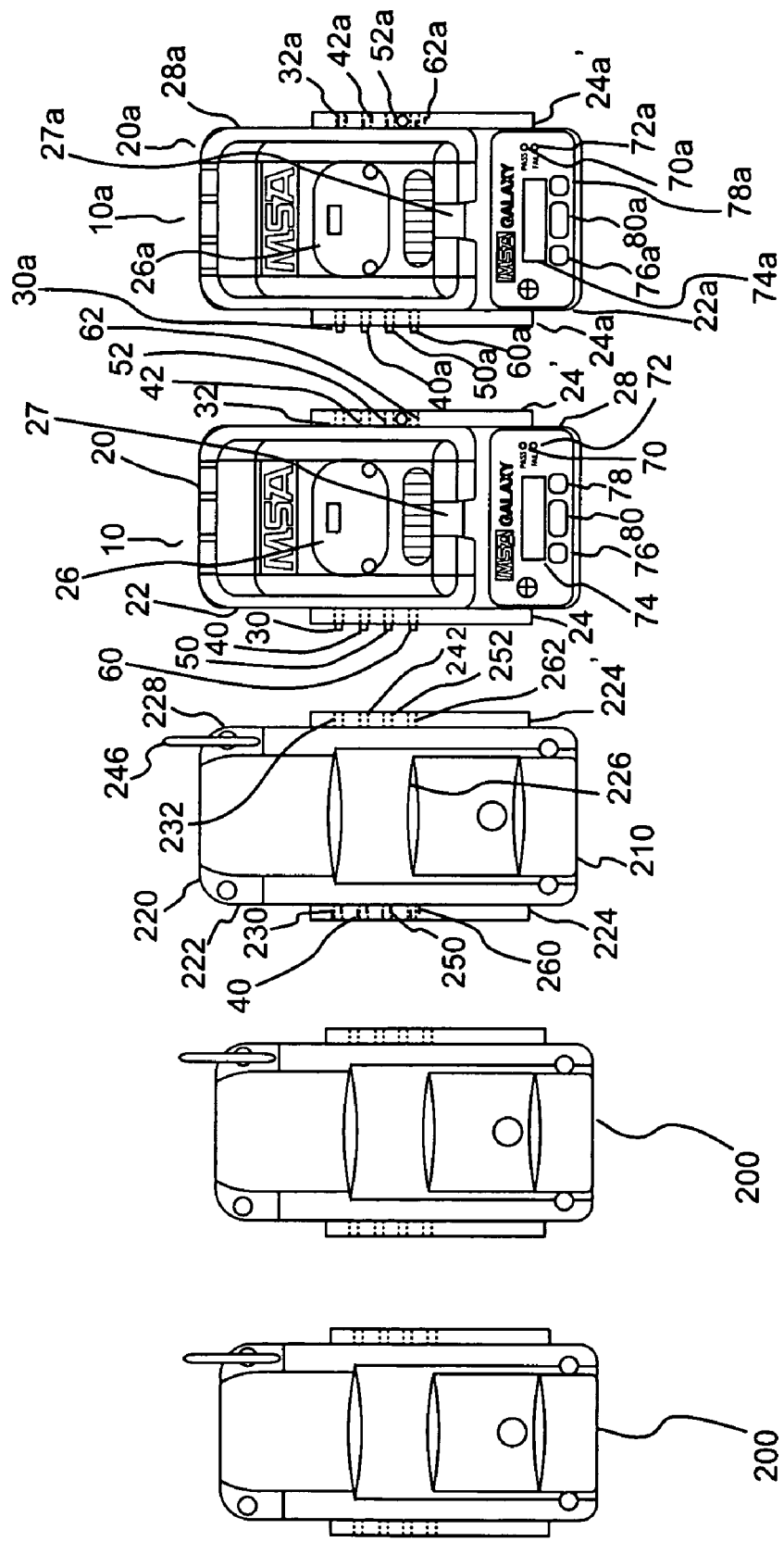
FIG. 5A illustrates a front view of the testing system of FIG. 4.
Figure 5B:
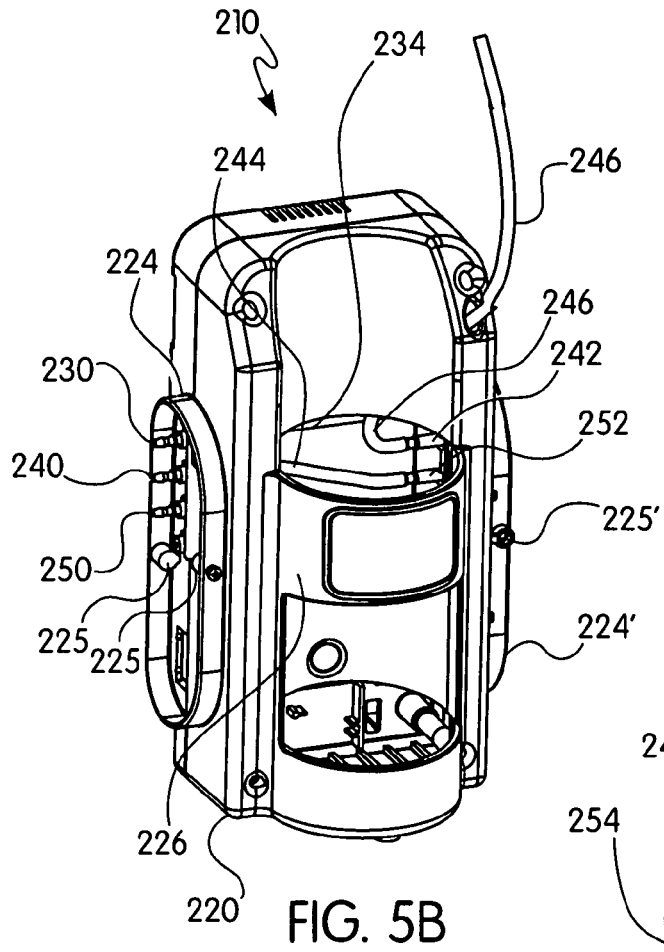
FIG. 5B illustrates a side perspective view one of the gas container modules of FIG. 5A.
Figure 5C:
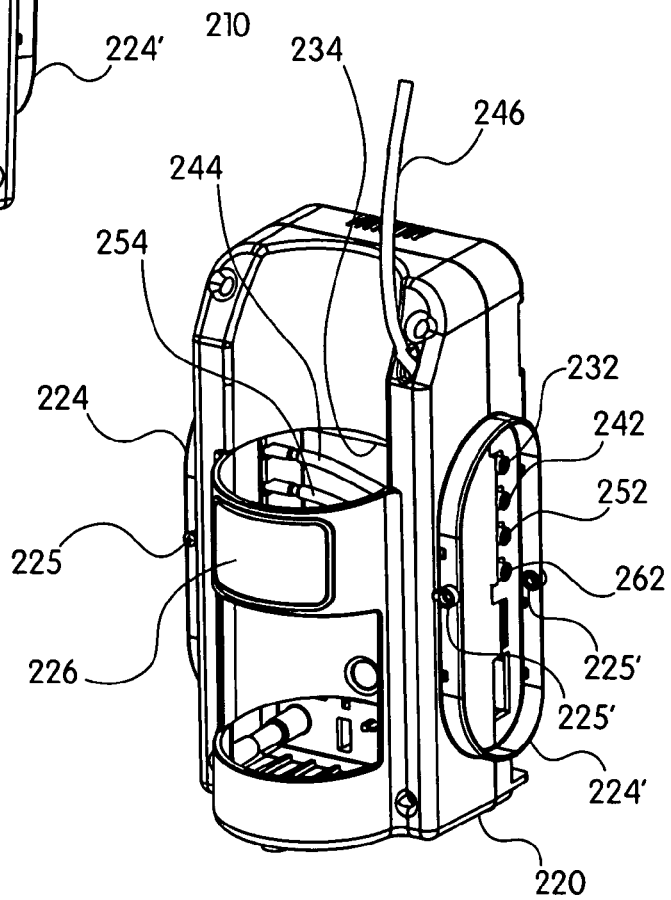
FIG. 5C illustrates a side perspective view one of the gas container modules of FIG. 5A from the opposite side of FIG. 5B.

FIG. 3A illustrates a second side 28 of housing 20. As illustrated in FIG. 3A, testing module 10 includes four outlets 32, 42, 52 and 62, which can, for example, include cooperating connectors or ports suitable to form a fluid connection with the ⅛ inch barbed connectors (or other connectors) so as to form a generally sealed fluid connection with inlets 30, 40, 50 and 60, respectively, of a second like testing module 10a (see, for example, FIG. 5A). Outlets 32, 42, 52 and 62 are surrounded by a connecting flange 24'.

Figure 4:
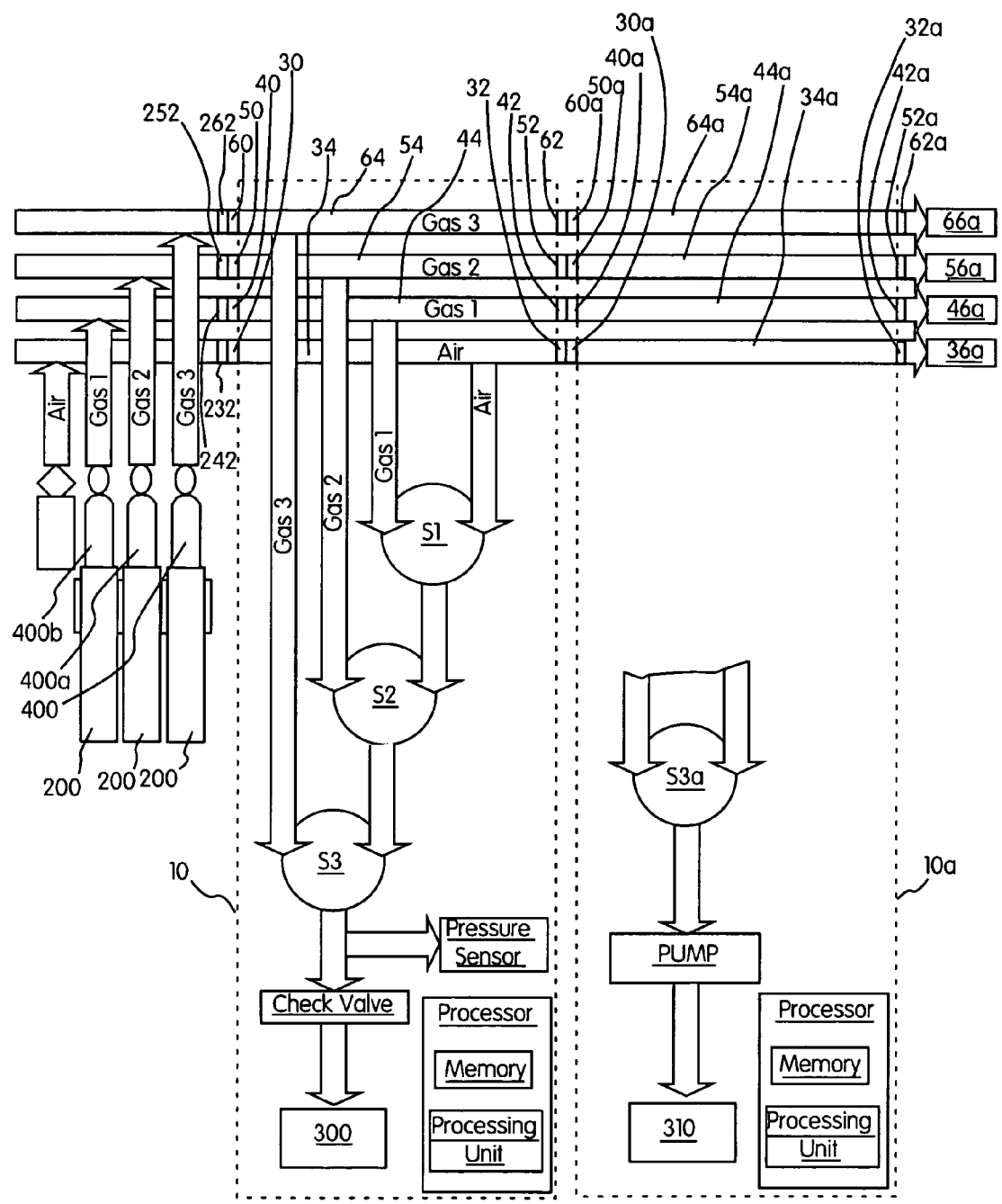
FIG. 4 illustrates a schematic diagram of an embodiment of a testing system of the present invention in which three gas container modules of the present invention and two testing modules of the present invention are connected in series.

As illustrated in, for example, FIG. 4, first inlet 30 is in fluid connection with first outlet 32 via fluid path or conduit 34, second inlet 40 is in fluid connection with second outlet 42 via fluid path or conduit 44, third inlet 50 is in fluid connection with third outlet 52 via fluid path or conduit 54, and fourth inlet 60 is in fluid connection with fourth outlet 62 via a fluid path or conduit 64. FIG. 4 is a representative and somewhat idealized schematic diagram illustrating flow elements, paths and connections of an embodiment of a testing system of the present invention. The relative dimensions and positions of such flow element, paths and connection are not representative of such dimensions and positions as, for example, illustrated in other figures herein.

Testing module 10 can operate alone or in connection with one or more other testing modules. As illustrated, for example, in FIGS. 4 and 5A, testing module 10 can be connected to another testing module 10a which includes a like housing 20a. In several embodiments, the exterior housings of the testing modules of the present invention were identical. However, the physical and electrical connections within different housings can be different to operate with different gas detectors. Likewise, the flow path from the test gas flow conduits within the housing to the gas detector to be tested can vary between testing modules. For example, in FIG. 4, testing module 10 is designed to operate with a gas detector 300 in which test gas reaches a sensor or sensors within gas detector 300 via forced flow created by a pump (not shown) within gas detector 300. As illustrated in FIG. 4, a pressure sensor can be placed in fluid connection with the flow path to the gas detector to ensure that the gas detector pump is operating correctly. Testing module 10a (for which, the fluid path from conduits 34a, 44a, 54a, and 64a is shown only partially) includes a pump in the flow path to a detector 310 seated therein to ensure the flow of test gas to the detector 310 in which (during field operation) test gas reaches a sensor or sensors within gas detector 300 via diffusion flow. In the embodiment illustrated, for example, in FIG. 4, solenoid controlled valves S1, S2 and S3 of testing module 10 are used in a manner known in the flow control arts to control which gas flows to gas detector 300. Various gas detectors, including, for example, the SOLARIS® Datalogging Multigas Detector, the SIRIUS® Multigas Detector and the ORION® Datalogging Multigas Detector, all available from Mine Safety Appliances Company, have been tested using the systems of the present invention. In such detectors, air can be used as a control or comparison gas during calibration.

In testing modules 10 and 10a as illustrated in FIG. 4, the flow paths within the testing modules between gas flow conduits 34, 44, 54 and 64 and gas detector 300 and between 34a, 44a, 54a and 64a and gas detector 310 include connections to each flow conduit. However, one or more testing modules of the present invention can be provided in which the flow path within the testing module between the test gas flow conduits and the gas detector does not have connections to all the test gas flow conduits.

As illustrated in FIG. 4, each testing module can be provided with a controller. Software for operation of the testing module can, for example, be stored in a memory that is in operative connection with a microprocessor. Data can, for example, be input into a software program of a testing module to, among other things, define which test gas flow conduit includes the appropriate test gas to be used in testing the gas detector that is operably connected to the testing module.

In general, like components of testing module 10a are numbered similarly to corresponding components of testing module 10 with the addition of the designation "a". When testing module 10 is in operative connection with testing module 10a, as illustrated, for example, in FIGS. 4 and 5A, outlets 32, 42, 52 and 62 of testing module 10 are placed in fluid connection with inlets 30a, 40a, 50a and 60a, respectively, of testing module 10a enabling gas to pass freely from conduits 34, 44, 54 and 64 to conduits 34a, 44a, 54a and 64a, respectively. Should testing module 10a be the last in a series of connected testing modules, flow terminators 36a, 46a, 56a and 66a (for example, rubber caps) can be placed upon outlets 32a, 42a, 52a and 62a, respectively, as illustrated in FIG. 4. Alternatively, another testing module (not shown) can be attached to testing module 10a by connecting the inlets of the additional testing module to outlets 32a, 42a, 52a and 62a of testing module 10a. As an alternative to the use of flow terminators, normally closed check valves (not shown) as known in the art can be provided in fluid connection with the outlets of each testing module. In general, the outlet check valves of a first testing module remain closed until inlets of a second like testing module are mated with, and thereby placed in fluid connection with, the outlets of the first testing module.

Flange 24' of testing module 10 is adapted to connect to flange 24a of testing module 10a. Flanges 24' and 24a can be secured using a connector (for example, a screw which passes through aligned holes 25' and 24a in flanges 24' and 24a, respectively) to secure the connection between testing module 10 and testing module 10a. In addition to providing a secure connection, cooperating flanges 24' and 24a also act to protect connected elements (for example, flow elements such as the inlets and outlets described above, intermodule communication elements and intermodule power elements) encompassed thereby.

By connecting testing modules of the present invention in series as described above, sensors of multiple gas detectors can be tested (for example, in an automated, simultaneous fashion) using multiple sources of test gas which are attached to the inlets of the first testing module of the series of testing modules. As illustrated, for example, in FIGS. 4 through 7B, in several embodiments of the present invention, one or more gas container or gas cylinder holding modules 210 are used to deliver test gas and/or air to one or more of the testing modules of the present invention. As illustrated, for example, in FIG. 7A, in one embodiment, gas container module 210 includes a housing 220 supporting four inlet connectors 230, 240, 250 and 260 on a first side 222 thereof. Inlets connectors 230, 240, 250 and 260 can, for example, include ⅛ inch barbed connectors as known in the gas connection arts. As described more fully below, inlet connector 260 does not operate as a gas inlet, but only as a connector when connecting to another like gas container module. Inlet connectors 230, 240, 250 and 260 are referred to generally herein as inlets. Inlets 230, 240, 250 and 260 are positioned in generally the same configuration as inlets 30, 40, 50 and 60 of testing module 10 (as well as in generally the same configuration as the inlets of other like testing modules). Inlet connectors 230, 240, 250 and 260 are surrounded by a connecting flange 224 including connecting elements 225 (for example, screw holes).

Gas container module 210 also includes four outlet connectors or outlets 232, 242, 252 and 262 on a second side 228 thereof. Outlets 232, 242, 252 and 262 can, for example, include connectors suitable to form a fluid connection with the barbed connectors of inlets 230, 240, 250 and 260 of another gas connector module or with the barbed connectors of inlets 30, 40, 50 and 60 of testing module 10 (or with the inlets of another like testing module of the present invention). Outlets 232, 242, 252 and 262 are positioned in generally the same configuration as outlets 32, 42, 52 and 62 of testing module 10 (as well as in generally the same configuration as the outlets of other like testing modules). Outlets 232, 242, 252 and 262 are surrounded by a connecting flange 224' including connecting elements 225' (for example, screw holes).

Figure 8A:
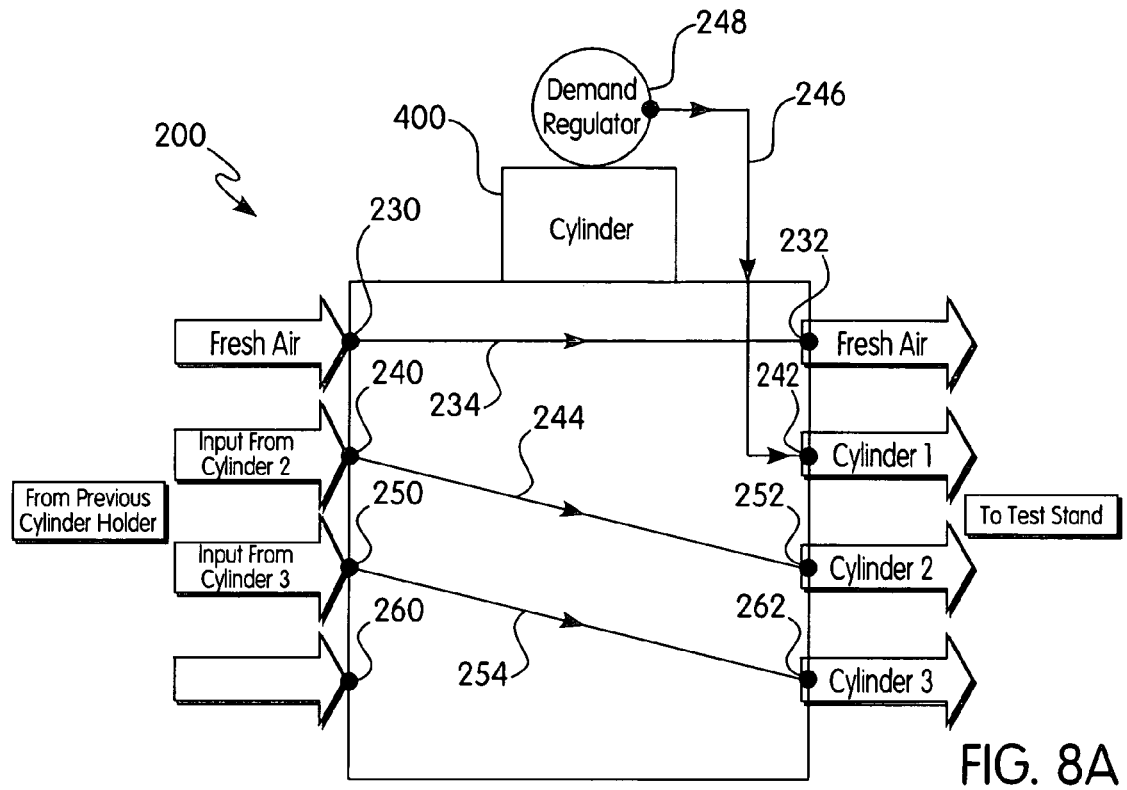
FIG. 8A illustrates a schematic diagram of gas flow through a gas container module of the present invention.
Figure 8B:
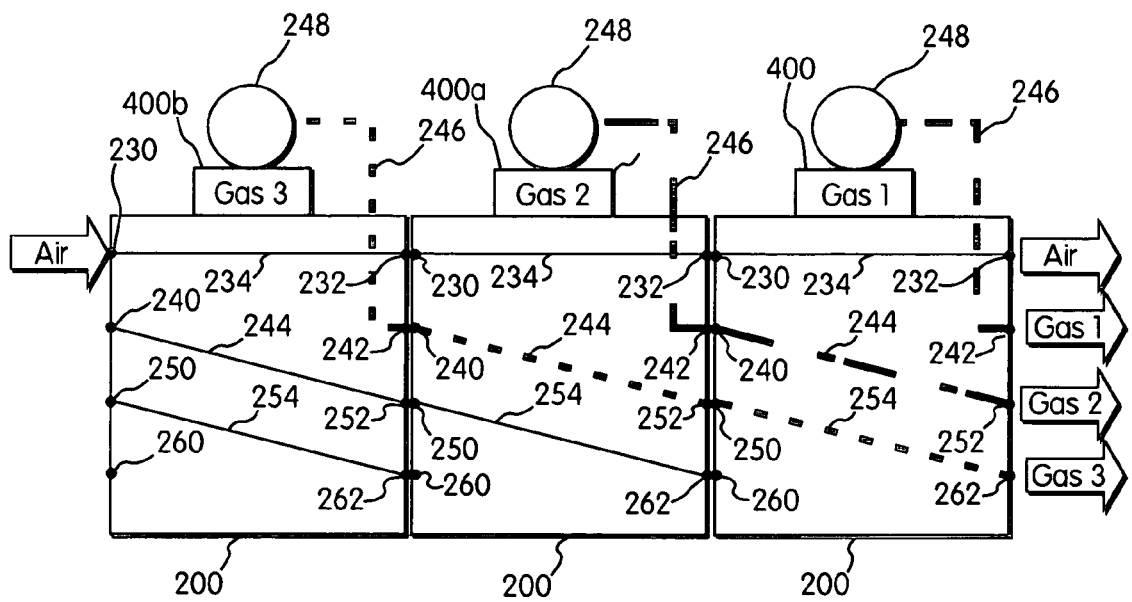
FIG. 8B illustrates a schematic diagram of gas flow through three gas containers modules of the present invention connected in series.

In one embodiment as illustrated in FIGS. 8A and 8B, inlet 230 is connected to outlet 232 via a fluid path or conduit 234. Outlet 242 is in fluid connection with a conduit 246 (for example, flexible tubing) at a first end of conduit 246. At a second end, conduit 246 is in fluid connection with a demand regulator 248 (see, for example, FIGS. 3A, 8A and 8B), which is adapted to be connected to a pressurized gas cylinder 400 as known in the art. Housing 220 of gas container module 210 includes a retainer 226 that can be shaped and dimensioned to securely hold gas cylinder 400 therein. Inlet 240 is connected to outlet 252 via a fluid path or conduit 244. Inlet 250 is connected to outlet 262 via a fluid path or conduit 254. Final inlet 260 includes a cooperating connector as described above, but is not connected to any fluid path or outlet. Once again, bottom or final inlet 260 operates merely as a connector to mate with outlet 262 of another gas container module 210 and can be excluded in an alternative embodiment. Indeed, in FIG. 5B, gas container module 210 is illustrated without inlet 260.

In the illustrated embodiment, conduit 234 of connected gas container modules 210 (via connected inlets 230 and outlets 232) transport air to conduits 34 and 34a of testing modules 10 and 10a, respectively. Gas container module 210 for test gas 1 (contained in cylinder 400) is attached to first testing module 10 of the series of connected testing modules. In each of gas container modules 210, the test gas cylinder connected thereto is in fluid connection with second (counting outlet 232 as the first merely for reference) outlet 242. In the case of gas container module 210 for test gas 1 (subsequently referred to as first gas container module 210) connected to first testing module 10 of the series of connected testing modules, second outlet 242 is connected to second (counting inlet 30 as the first) inlet 40 of testing module 10, thereby transporting test gas 1 through second conduits 44 and 44a of testing modules 10 and 10a, respectively. As second inlet 240 of each of gas container modules 210 is in fluid connection with third outlet 252 thereof via conduit 244, test gas 2 is transported from outlet 242 of second gas container module 210 (through inlet 240 and conduit 244 of first gas container module 210) to third outlet 252 of first gas container module 210, and thereby through third conduits 54 and 54a of testing modules 10 and 10a, respectively. Once again, as second inlet 240 of each of gas container modules 210 is in fluid connection with third outlet 252 thereof via conduit 244, test gas 3 is transported from outlet 242 of third gas container module 210 (through inlet 240 and conduit 244 of second gas container module 210) to third outlet 252 of second gas container module 210, and thereby through third inlet 250 of first gas container module 210. As third inlet 250 of each of gas container modules 210 is in fluid connection with fourth outlet 262 thereof via conduit 254, test gas 3 is transported from third inlet 250 of first gas container module 210 (through conduit 254 of first gas container module 210) to fourth outlet 262 of first gas container module 210, thereby transporting test gas 3 through fourth conduits 64 and 64a of testing modules 10 and 10a, respectively.

This cascading flow algorithm can be repeated for additional gas container modules connected in series (and further, to additional testing modules connected in series) simply by providing more inlets, outlets and connecting conduits. In the case of the gas container modules, the first inlet and outlet can be dedicated to the flow of ambient air. Likewise, the second outlet of a gas container module can be dedicated to the flow of gas from a gas cylinder in operative connection with that gas container module. For the second inlet, third inlet, fourth inlet etc., a fluid connection can be made between the inlet and the subsequent outlet (that is, the third outlet, fourth outlet, fifth outlet etc., respectively). In other words, referring to, for example, the second inlet as $I_2$ and the third outlet as $O_3$, inlet $I_i$ is in fluid connection with outlet $O_{i+1}$ for each gas container modules wherein x is greater than or equal to 2. For a total of X+1 outlets, there need be only X inlets as one outlet is dedicated to the gas container seated in the gas container module.

In the illustrated embodiments, the resulting "cascading" flow through a plurality of gas container modules connected in series results in ambient air being transported through outlet $O_1$ of the first gas container module (that is, the gas container module connected to the first of the series of testing modules). Gas Y is transported through outlet $O_{y+1}$ of first gas container module, wherein Y designates the position of the gas container module in the series of connected gas container modules (that is, Y is 1 for the first gas container module, 2 for the second gas container module etc.).

Of course, other flow configuration can be used. For example, the last inlet/outlet pair can be dedicated to air, and cascading flow can occur in the inlets and outlets above the air flow. The air flow inlet/outlet pair can also be positioned elsewhere. Moreover, virtually any geometry or configuration other than a generally linear alignment of inlets/outlets can be used. For example, inlets and outlets can be placed in a generally circular arrangement with cascading flow occurring around the circle in a manner as generally described above.

In one embodiment, each of the testing modules of the present invention is provided with a power connection, which can be powered via AC power form a power outlet. DC power can be provided, for example, from a vehicle module connectible to a vehicle battery or via DC power from a battery back 90 as illustrated, for example, in FIGS. 1 and 3A. In this embodiment, battery pack 90 includes four batteries 92a, 92b, 92c and 92d (which can be rechargeable) retained within battery back 90 via a retainer 94. An electrical connector 96 on battery pack 90 forms an electrical connection with a cooperating connector 82 (see FIGS. 1 and 3A) of testing module 10 (or a like testing module). The housing of battery pack 90 is adapted to connect to flange 24' of testing module 10 in a manner similar to that described above for connection of flange 24' to flange 24a. In certain embodiments, battery pack 90 can be used in connection with only a single testing module. However, suitable electrical power connections can be provided between testing modules so that a single battery pack can power multiple testing modules connected in series.

Testing module 10 (and like testing modules) can be provided with a communication slot 84 into which a memory card 86 (see FIGS. 1 and 3A) can be placed in communicative connection. Memory card 86 (which can be in communicative connection with the microprocessor of the testing module) can, for example, provide data storage and print record capability in addition to that available in testing module 10 without memory card 86. In the case that a battery pack 90 or a network interface 120 (see FIGS. 6A and 6B) as described below is not installed, an end cap 110 (see FIG. 3B) is preferably placed in connection with flange 24'. End cap 110 can, for example, provide protection for memory card 86 and other components positioned within the confines of flange 24'.

Figure 6A:
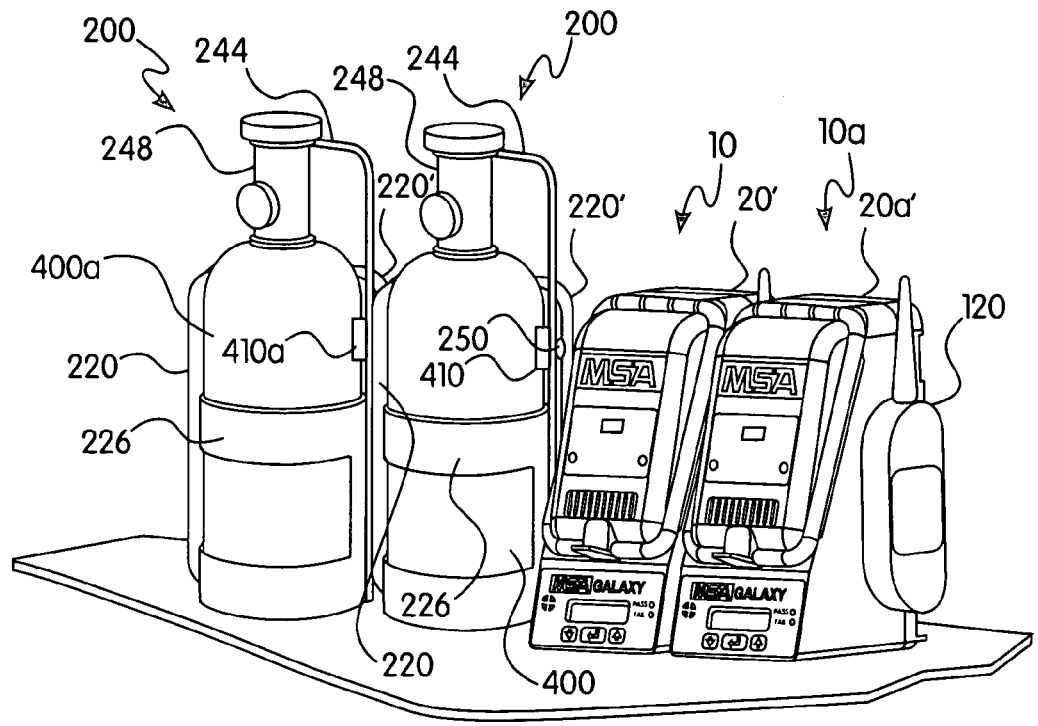
FIG. 6A illustrates a perspective view of an embodiment of a testing system of the present invention resting on a surface in which two gas container modules and two testing modules are connected in series, and a network communication module is connected to the end or last testing module of the series.
Figure 6B:
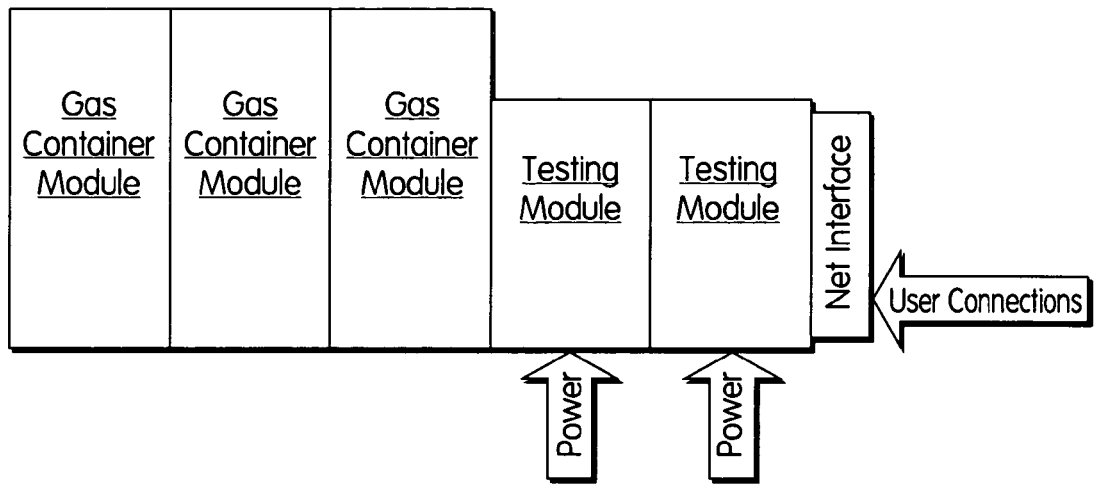
FIG. 6B illustrates a schematic diagram of the testing system of FIG. 6A.
Figure 7B:
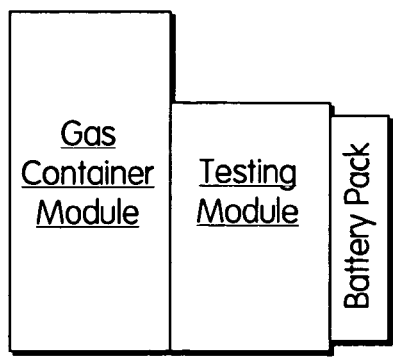
FIG. 7B illustrates a schematic diagram of a gas container module of the present invention connected to a testing module of the present invention, to which a battery pack is connected.
Figure 7A:
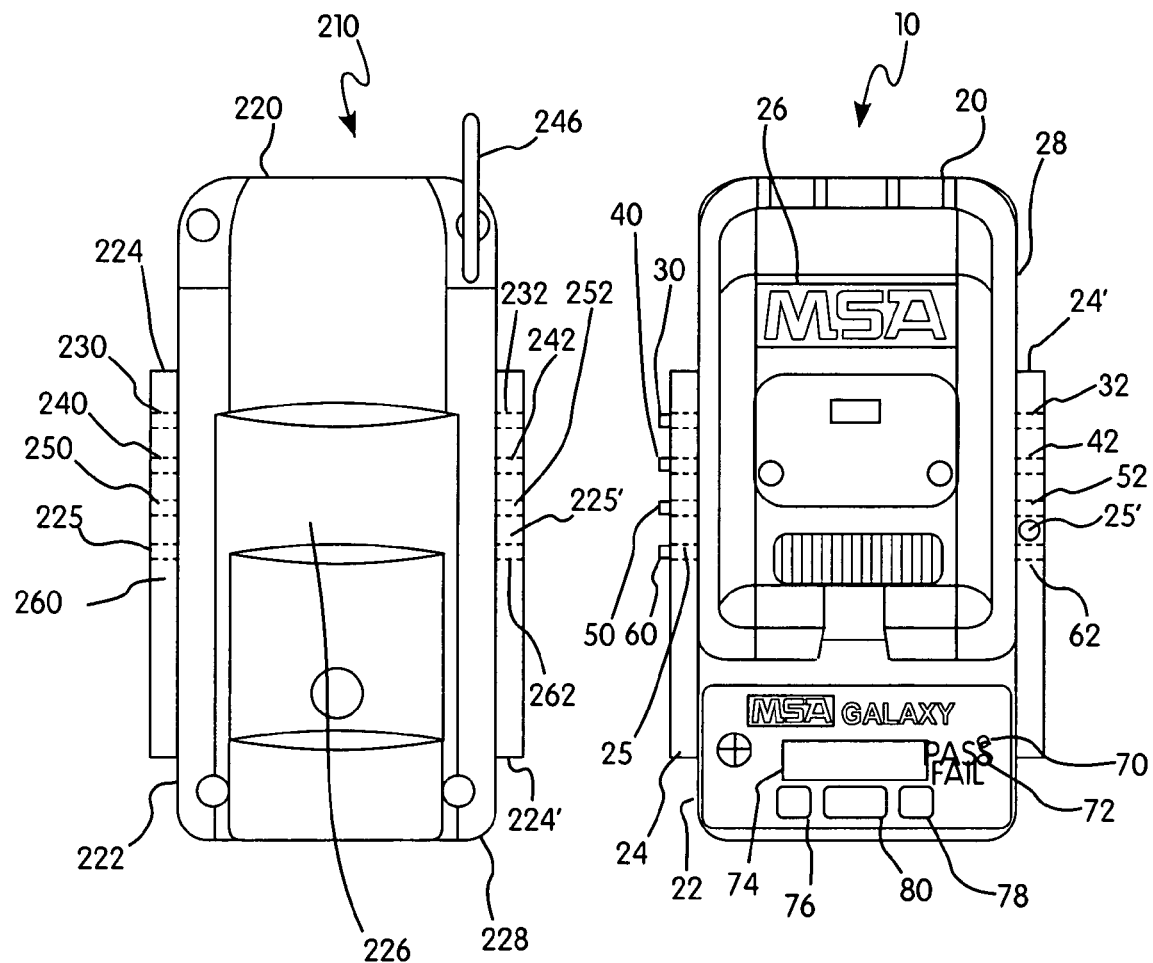
FIG. 7A illustrates a front view of a gas container module of the present invention in alignment for connection to a testing module of the present invention.
Figure 9:
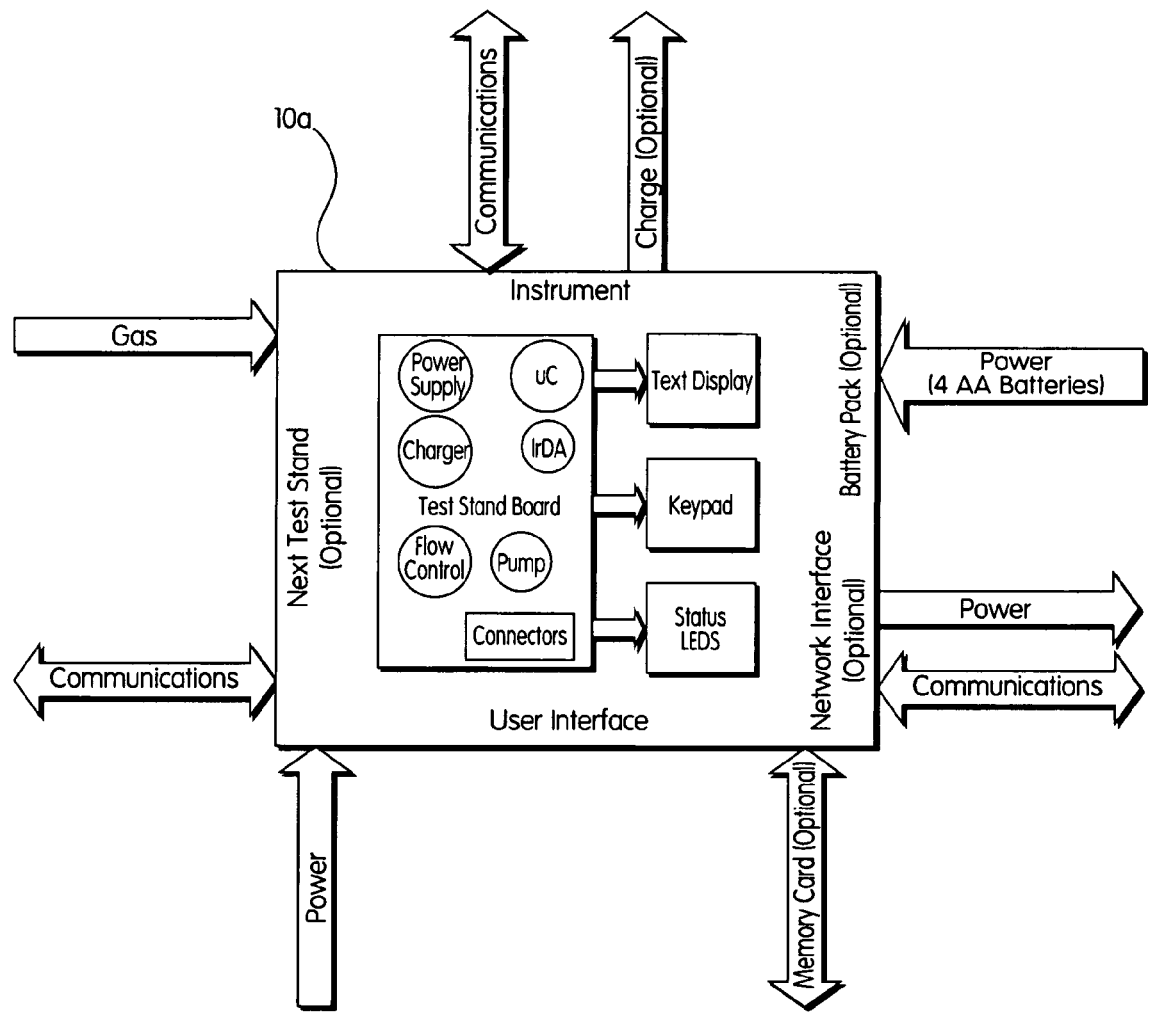
FIG. 9 illustrates a schematic diagram of a testing module of the present invention showing, among other things, communication paths between connected testing modules, between a testing module and a gas detector in operative connection with the testing module, between a testing module and a connected memory card and between a testing module and a network via a network interface.

As illustrated, for example, in FIG. 9, communication connections are provided between a testing module and the gas detector in operative connection therewith as well as between connected testing modules of the present invention. Using such communication connections, a single memory card 86 can communicate with a plurality of testing modules connected in series. Likewise, as illustrated in FIGS. 6A and 6B, a network module 120 can be placed in communicative connection via a communication port 89 (see FIG. 3A) with the last testing module of a series of connected testing modules to provide network communication (either wireless or wired network communications as known in, for example, the computer arts) with all testing modules of the series. Communication port 89 and a cooperating communication port 89' (see, for example, FIGS. 1, 2A and 2B0 can also be used to effect communication between connected testing modules.

In a similar manner, communication can be provided between gas container modules 200 which are connected in series and/or between gas container modules 210 and testing modules 10, 10a, etc. or other networked components. Communication from gas container modules 200 can, for example, be desirable in the case that gas container modules 210 include one or more sensors 250 adapted to read data from one or more indicators 410 and 410a on gas containers 400 and 400a, respectively, as illustrated in FIG. 6A. Indicators 410 and 410a can, for example, provide data on the composition, pressure, volume etc. of gas contained therein, which can be read by one or more sensors 250 of gas container modules 210 and, for example, communicated to testing modules 10 and/or 10a. Indicators 410 and 410a can, for example, be RFID (radio frequency identification) tags. Alternatively, indicators 410 and 410a can be optical bar indicators as known in the art, in which case, sensors 250 can be optical scanners as known in the art. Likewise, many other indicator/sensor pairs are suitable for use in the present invention.

Figure 10:
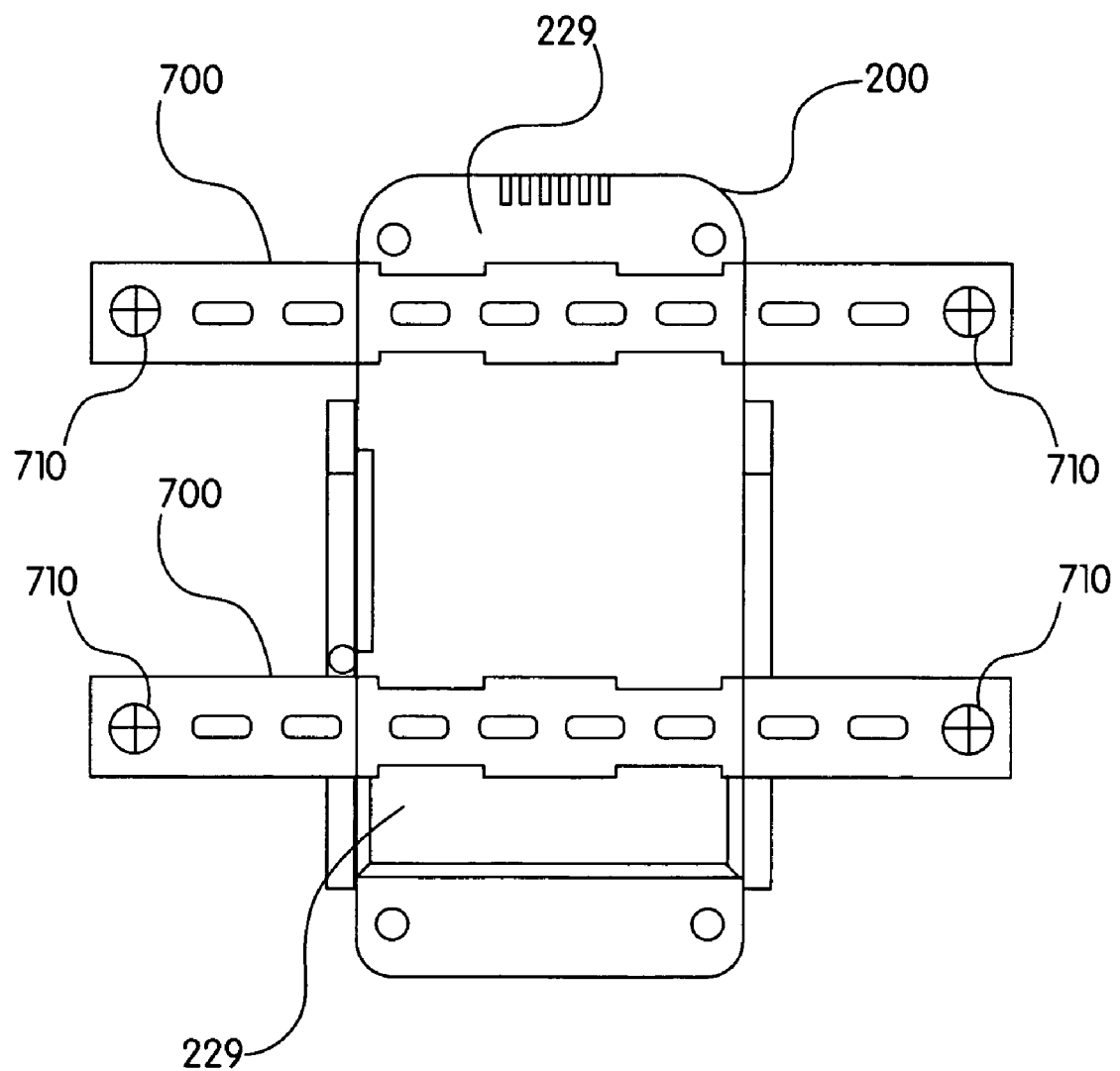
FIG. 10 illustrates a gas container module of the present invention in operative connection with a pair of DIN rails for mounting on a vertical surface.

As best illustrated in FIG. 6A, the bottoms of the testing modules and the gas container modules of the present invention can be made to be sufficiently flat to enable use of the gas testing systems of the present invention on a table 600 or other surface. Furthermore, the rearward side of the testing modules and gas container modules of the present invention can be formed with appropriated cooperating connectors to allow attachment thereof to one or more DIN rails. In FIG. 10, for example, gas container module 210 is illustrated with connectors 229 on a rearward side thereof to connect gas container module 210 to DIN rails 700. DIN rails 700 can, for example, be mounted on a wall using mounts 710 as known in the art.

In several embodiments of the present invention, the rearward or back portions or sections of the housings for the testing modules and the gas container modules (which include the inlets, outlet, communication ports etc.) were fabricated to be generally identical (see, for example, FIGS. 1, 3A, 5B and 5C. Different front section where then attached to the back sections to form the testing modules and the gas container modules.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A testing module for use with a gas detector, comprising:
   a housing;
   a seating connected to the housing and adapted to operably connect the gas detector to the testing module;

a plurality of gas inlets connected to the housing, each gas inlet adapted to pass a gas therethrough;

a plurality of gas outlets connected to the housing, each gas outlet being in fluid connection with one of the gas inlets; and the plurality of gas outlets being configured on the housing in generally the same configuration as the plurality of inlets are configured on the housing and each of the plurality of outlets being adapted to mate with and form a fluid connection with one of a plurality of inlets of a second like testing module, wherein once such fluid connections are made, gases can flow from the outlets of the testing module into the inlets of the second like testing module.

2. The testing module of claim 1 further comprising a communication system to receive information and to transmit information.

3. The testing module of claim 2 wherein the communication system is provided to transmit and receive communications between the testing module and the second like testing module when connected.

4. The testing module of claim 1 further comprising a data input system and a data output system.

5. The testing module of claim 1 further comprising a flow control system adapted to provide flow from at least one of the plurality of gas inlets to the gas detector.

6. The testing module of claim 1 wherein the plurality of gas inlets are configured in a generally linear configuration.

7. The testing module. of claim 1 wherein each of the plurality of inlets comprises a barbed connector.

8. A gas detector testing system, comprising:
at least one testing module for use with a gas detector, comprising:
  a testing module housing;
  a gas detector seating connected to the testing module housing and adapted to operably connect the gas detector to the testing module;
  a plurality of inlets connected to the testing module housing, each inlet of the at least one testing module being adapted to pass a gas therethrough;
  a plurality of outlets connected to the testing module housing, each outlet of the at least one testing module being in fluid connection with one of the gas inlets of the at least one testing module; and
  the plurality of outlets of the at least one testing module being configured on the testing module housing in generally the same configuration as the plurality of inlets of the at least one testing module are configured on the testing module housing and each of the plurality of outlets of the at least one testing module being adapted to mate with and form a fluid connection with one of a plurality of inlets of a second like testing module, wherein once such fluid connections are made, gases can flow from the plurality of outlets of the at least one testing module into the plurality of inlets of the second like testing module; and
at least one gas container module for use with a gas container, comprising:
  a gas container module housing;
  a gas container seating connected to the gas container module housing and adapted to receive the gas container,
  a plurality of gas inlets connected to the gas container module housing, each of the plurality of gas inlets of the at least one gas container module being adapted to pass a gas therethrough;
  a plurality of gas outlets connected to the gas container module housing, each of the plurality of gas inlets of the at least one gas container module being in fluid connection with one of the plurality of gas outlets of the at least one gas container module; and
  the plurality of gas inlets of the at least one gas container module being configured on the gas container housing in generally the same configuration as the plurality of gas outlets of the at least one gas container module are configured on the gas container housing and each of the plurality of gas inlets of the at least one gas container module being adapted to mate with and form a fluid connection with one of a plurality of gas outlets on a gas container housing of a second like gas container module, wherein once such fluid connections are made, gases can flow from the plurality of gas outlets of the second like gas container module into the plurality of gas inlets of the at least one gas container module;
  the plurality of inlets of the at least one testing module being configured on the testing module housing in generally the same configuration as the plurality of gas outlets of the at least one gas container module are configured on the gas container module housing and each of the plurality of inlets of the at least one testing module being adapted to mate with and form a fluid connection with one of the plurality of gas outlets of the at least one gas container module, wherein once such fluid connections are made, gases can flow from the plurality of gas outlets of the at least one gas container module into the plurality of gas inlets of the at least one testing module.

9. The system of claim 8 wherein the at least one gas container module further comprises a gas container conduit in fluid connection with one of the gas outlets of the at least one gas container module at a first end, the at least one gas container conduit being adapted to form a connection with the gas container at a second end thereof.

10. The system of claim 9 further comprising a demand regulator in fluid connection with the second end of the gas container conduit.

11. The system of claim 9 wherein the at least one gas container module comprises at least X gas inlets $I_1$ through $I_x$ and at least X+1 gas outlets $O_1$ though $O_{x+1}$, wherein the first end of the container conduit is in fluid connection with gas outlet $O_1$, and each gas inlet $I_i$, is in fluid connection with gas outlet $O_{i+1}$.

12. The system of claim 11 wherein the at least one gas container module comprises two gas inlets $I_1$ and $I_2$ and at least three outlets $O_1$ through $O_3$,
wherein the first end of the gas container conduit is in fluid connection with outlet $O_2$, inlet $I_1$ is in fluid connection with $O_2$ and inlet $I_2$ is in fluid connection with outlet $O_3$.

13. The system of claim 12 wherein the outlet $O_1$ is adapted to mate with and form a fluid connection with gas inlet $I_1'$ of the second like gas container module and outlet $O_2$ is adapted to mate with and form a fluid connection with gas inlet $I_2'$ of the second like gas container module.

14. The system of claim 13 further comprising a connector to mate with and form a connection with outlet $O_3$.

15. The system of claim 12 wherein the at least one gas container module further comprises an air inlet connected to the housing of the at least one gas container module and being in fluid connection with an air outlet connected to the housing of the at least one gas container module, the air inlet being adapted to mate and form a fluid connection with an air inlet of the second like gas container module.

16. The system of claim 8 wherein the at least one gas container module further comprises a communication system.

17. The system of claim 16 further comprising a sensor in communicative connection with the communication system of the at least one gas container module, the sensor being adapted to read data from the gas container.

18. The system of claim 8 wherein the plurality of gas inlets of the at least one gas container module are arranged in a series on a first section of the housing of the at least one gas container module and the plurality of outlets of the at least one gas container module are arranged in a series in a second section of the housing of the at least one gas container module, the at least one gas container module further comprising a container conduit in fluid connection with one of the plurality of gas outlets of the at least one gas container module at a first end, the container conduit being adapted to form a connection with the gas container at a second end thereof, each of the plurality of gas inlets of the at least one gas container module being in fluid connection with one of the plurality of gas outlets of the at least one gas container module such that when a plurality of like gas container modules are connected in a series, a gas exiting each gas outlet of the at least one gas container module is determined by a position in the series of gas container modules of the one of the gas container modules seating a corresponding gas container.

19. The system of claim 8 wherein the at least one testing module further comprises a communication system to receive information and to transmit information.

20. The system of claim 19 wherein the communication system of the at least one testing module is provided to transmit and receive communications between the at least one testing module and the second like testing module when connected.

21. The system of claim 8 wherein the at least one testing module further comprises a data input system and a data output system.

22. The system of claim 8 wherein the at least one testing module further comprises a flow control system adapted to provide flow from at least one of the plurality of gas inlets to the gas detector.

23. The system of claim 8 wherein the plurality of gas inlets of the at least one testing module, the plurality of gas outlets of the at least one testing module, the plurality of gas inlets of the at least one gas container module and the plurality of outlets of the at least one gas container module are configured in a generally linear configuration.

* * * * *

UNITED STATES PATENT AND TRADEMARK OFFICE
CERTIFICATE OF CORRECTION

PATENT NO. : 7,530,255 B2  
APPLICATION NO. : 11/171861  
DATED : May 12, 2009  
INVENTOR(S) : William R. Frank, Daniel E. Bruce and Jon K. Haverstick Page 1 of 1

It is certified that error appears in the above-identified patent and that said Letters Patent is hereby corrected as shown below:

Add to the title cover item: Related U.S. Application Data - Provisional application No. 60/644,647 filed on 01/18/2005.

Signed and Sealed this

First Day of September, 2009

David J. Kappos
*Director of the United States Patent and Trademark Office*